US012690817B2

(12) United States Patent
Barve et al.

(10) Patent No.: US 12,690,817 B2
(45) Date of Patent: Jul. 28, 2026

(54) APPARATUS AND METHOD FOR SUBJECT MONITORING AND DIAGNOSING WITH NON-INVASIVE MEASURES

(71) Applicant: Anumana, Inc., Cambridge, MA (US)

(72) Inventors: Rakesh Barve, Bengaluru (IN); Samir Awasthi, Boston, MA (US); Abhijith Chunduru, Bengaluru (IN); Suthirth Vaidya, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/907,123

(22) Filed: Oct. 4, 2024

(65) Prior Publication Data

US 2026/0096783 A1     Apr. 9, 2026

(51) Int. Cl.
| | |
|---|---|
| *A61B 5/00* | (2006.01) |
| *A61B 5/256* | (2021.01) |
| *A61B 5/346* | (2021.01) |
| *A61B 8/00* | (2006.01) |
| *A61B 8/08* | (2006.01) |

(Continued)

(52) U.S. Cl.
CPC ............ *A61B 5/7267* (2013.01); *A61B 5/256* (2021.01); *A61B 5/346* (2021.01); *A61B 5/7246* (2013.01); *A61B 8/0883* (2013.01); *A61B 8/5261* (2013.01); *G06T 15/005* (2013.01); *G16H 50/20* (2018.01); *G16H 50/70* (2018.01); *A61B 8/463* (2013.01); *G06T 7/0012* (2013.01); *G06T 2207/10132* (2013.01);

(Continued)

(58) Field of Classification Search
None
See application file for complete search history.

(56) References Cited

U.S. PATENT DOCUMENTS

| | | | |
|---|---|---|---|
| 7,877,130 B2 | 1/2011 | O'Donnell et al. | |
| 2013/0281815 A1* | 10/2013 | Varadan | A61B 5/282 |
| | | | 600/388 |

(Continued)

FOREIGN PATENT DOCUMENTS

| | | |
|---|---|---|
| KR | 20140126994 A | 11/2014 |
| RU | 2508055 C2 | 2/2014 |

*Primary Examiner* — Benjamin J Klein
*Assistant Examiner* — Willow Grace Welch
(74) *Attorney, Agent, or Firm* — CALDWELL LLC

(57) ABSTRACT

An apparatus and method for subject monitoring and diagnosing with non-invasive measures are disclosed. The apparatus includes a memory contains instructions configuring at least a processor to generate invasive measurement training data, train an invasive measurement machine-learning model using the invasive measurement training data, receive non-invasive measurement data, wherein the non-invasive measurement data includes electrocardiogram (ECG) data and echocardiogram (echo) data and the non-invasive measurement data includes information that is obtained through non-invasive measurements, fuse the ECG data and the echo data into a fused non-invasive measurement datum, generate at least an invasive measurement datum as a function of the fused non-invasive measurement datum using the trained invasive measurement machine-learning model, wherein the at least an invasive measurement datum includes information that can be obtained through invasive measurements and transmitting the at least an invasive measurement datum to a remote device.

19 Claims, 8 Drawing Sheets

(51) Int. Cl.
| | |
|---|---|
| *G06T 7/00* | (2017.01) |
| *G06T 15/00* | (2011.01) |
| *G16H 50/20* | (2018.01) |
| *G16H 50/70* | (2018.01) |

(52) U.S. Cl.
CPC .............. *G06T 2207/20081* (2013.01); *G06T 2207/20084* (2013.01); *G06T 2207/30048* (2013.01)

(56) References Cited

U.S. PATENT DOCUMENTS

| | | | | |
|---|---|---|---|---|
| 2018/0333104 A1* | 11/2018 | Sitek | .................... | A61B 5/7267 |
| 2020/0128670 A1* | 4/2020 | Chong Rodriguez | . | A61B 5/329 |
| 2021/0308490 A1* | 10/2021 | Hu | ....................... | A61N 5/1049 |
| 2022/0189636 A1* | 6/2022 | Wagner | .................. | G16H 10/60 |
| 2024/0206821 A1* | 6/2024 | Upadhyay | .............. | A61B 5/318 |
| 2024/0350120 A1* | 10/2024 | Raschke | ............... | A61B 8/466 |

* cited by examiner

200

144

<          John Doe

CT Image 204

208    Possible Diagnosis:
            I. Arrhythmia

212    Need for Surgery: YES

700

705 Generating Invasive Measurement Training Data

710 Training Invasive Measurement Machine-learning Model

715 Receiving Non-invasive Measurement Data

720 Fusing ECG Data and Echo Data

725 Generating at Least an Invasive Measurement Datum

730 Transmitting the at Least an Invasive Measurement Datum

APPARATUS AND METHOD FOR SUBJECT MONITORING AND DIAGNOSING WITH NON-INVASIVE MEASURES

FIELD OF THE INVENTION

The present invention generally relates to the field of patient monitoring. In particular, the present invention is directed to an apparatus and method for subject monitoring and diagnosing with non-invasive measures.

BACKGROUND

Traditional diagnostic methods rely on clinicians' manual interpretation of various medical data types, including imaging, laboratory results, and patient histories. This manual approach, while valuable, is often limited by human cognitive capabilities, variability in expertise, and susceptibility to errors. The sheer volume and complexity of medical data generated in modern healthcare pose significant challenges for timely and accurate diagnosis.

SUMMARY OF THE DISCLOSURE

In an aspect, an apparatus for subject monitoring and diagnosing with non-invasive measures is disclosed. The apparatus includes at least a processor and a memory communicatively connected to the at least a processor, wherein the memory contains instructions configuring the at least a processor to generate invasive measurement training data, wherein the invasive measurement training data includes correlations between exemplary non-invasive measurement data correlated to exemplary invasive measurement datums, train an invasive measurement machine-learning model using the invasive measurement training data, receive non-invasive measurement data, wherein the non-invasive measurement data includes electrocardiogram (ECG) data and echocardiogram (echo) data and the non-invasive measurement data includes information that is obtained through non-invasive measurements, fuse the ECG data and the echo data into a fused non-invasive measurement datum, generate at least an invasive measurement datum as a function of the fused non-invasive measurement datum using the trained invasive measurement machine-learning model, wherein the at least an invasive measurement datum includes information that can be obtained through invasive measurements and transmitting the at least an invasive measurement datum to a remote device.

In another aspect, a method for subject monitoring and diagnosing with non-invasive measures is disclosed. The method includes generating, using at least a processor, invasive measurement training data, wherein the invasive measurement training data includes correlations between exemplary non-invasive measurement data correlated to exemplary invasive measurement datums, training, using the at least a processor, an invasive measurement machine-learning model using the invasive measurement training data, receiving, using the at least a processor, non-invasive measurement data, wherein the non-invasive measurement data includes electrocardiogram (ECG) data and echocardiogram (echo) data and the non-invasive measurement data includes information that is obtained through non-invasive measurements, fusing, using the at least a processor, the ECG data and the echo data into a fused non-invasive measurement datum, generating, using the at least a processor, at least an invasive measurement datum as a function of the fused non-invasive measurement datum using the trained invasive measurement machine-learning model, wherein the at least an invasive measurement datum includes information that can be obtained through invasive measurements and transmitting, using the at least a processor, the at least an invasive measurement datum to a remote device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and method for subject monitoring and diagnosing with non-invasive measures are disclosed. The apparatus includes at least a processor and a memory communicatively connected to the at least a processor, wherein the memory contains instructions configuring the at least a processor to generate invasive measurement training data, wherein the invasive measurement training data includes correlations between exemplary non-invasive measurement data correlated to exemplary invasive measurement datums, train an invasive measurement machine-learning model using the invasive measurement training data, receive non-invasive measurement data, wherein the non-invasive measurement data includes electrocardiogram (ECG) data and echocardiogram (echo) data and the non-invasive measurement data includes information that is obtained through non-invasive measurements, fuse the ECG data and the echo data into a fused non-invasive measurement datum, generate at least an invasive measurement datum as a function of the fused non-invasive measurement datum using the trained invasive measurement machine-learning model, wherein the at least an invasive measurement datum includes information that can be obtained through invasive measurements and transmitting the at least an invasive measurement datum to a remote device.

Aspects of this disclosure may significantly reduce patient exposure to radiation associated with medical imaging procedures, such as computed tomography (CT) or positron emission tomography (PET) scans. Additionally, aspects of this disclosure may be more cost effective than medical imaging procedures, such as CT, PET or magnetic resonance imaging (MRI) scans and reduce the risk to kidney harm associated with contrast agents used in the MRI scans. Furthermore, by eliminating the need for certain medical imaging processes, the overall medical diagnostic and treatment workflow may be streamlined, leading to a more efficient and less invasive patient care experience. Exemplary embodiments illustrating aspects of the present disclosure are described below in the context of several specific examples.

Figure 1:
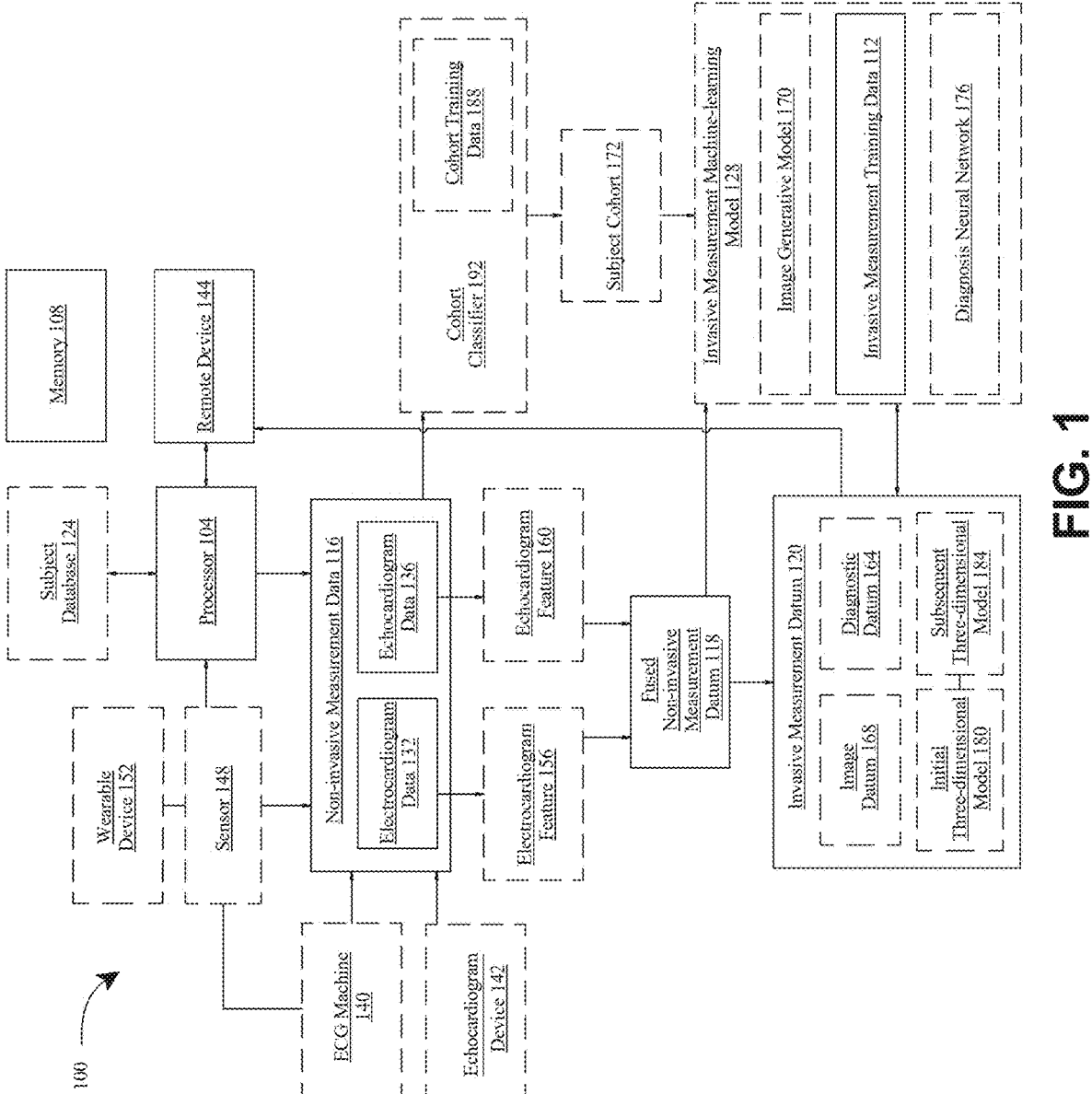
FIG. 1 illustrates a block diagram for subject monitoring and diagnosing with non-invasive measures.

Referring now to FIG. 1, an exemplary embodiment of an apparatus 100 for subject monitoring and diagnosing with non-invasive measures is illustrated. Apparatus 100 includes at least a processor 104. Processor 104 may include, without limitation, any processor described in this disclosure. Processor 104 may be included in a computing device. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory 108 communicatively connected to processor 104. For the purposes of this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 108 contains instructions configuring processor 104 to generate invasive measurement training data 112. invasive measurement training data 112 includes correlations between exemplary non-invasive measurement data correlated to exemplary invasive measurement datums. The non-invasive measurement data

116 and invasive measurement datum 120 are described in detail below. Processor 104 is configured to train an invasive measurement machine-learning model 128 using invasive measurement training data 112.

With continued reference to FIG. 1, for the purposes of this disclosure, "invasive measurement training data" is a set of data used to train an invasive measurement machine-learning model. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from subject database 124 or be provided by a user. In other embodiments, a machine-learning module may obtain a training set by querying a communicatively connected subject database 124 that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. Machine learning module may be used to generate a machine learning model and/or any other machine learning model using training data. Machine learning model may be trained by correlated inputs and outputs of training data. Training data may be data sets that have already been converted from raw data whether manually, by machine, or any other method. Training data may be stored in subject database 124. Training data may also be retrieved from subject database 124. In some embodiments, invasive measurement training data 112 may be received from one or more users, subject database 124, external computing devices, and/or previous iterations of processing. As a non-limiting example, invasive measurement training data 112 may include instructions from a user, who may be an expert user, a past user in embodiments disclosed herein, or the like, which may be stored in memory and/or stored in subject database 124, where the instructions may include labeling of training examples. In some embodiments, processor 104 may retrieve invasive measurement training data 112 from a database of a health organization, hospital, and the like or electronic health record (EHR) system. For the purposes of this disclosure, an "electronic health record" is the systematized collection of subject and population electronically stored health information in a digital format. In some embodiments, invasive measurement training data 112 may be updated iteratively using a feedback loop. As a non-limiting example, processor 104 may update invasive measurement training data 112 iteratively through a feedback loop as a function of user cohort, non-invasive measurement data 116, electrocardiogram (ECG) data 132, echocardiogram (echo) data 136, input and output of invasive measurement machine-learning model 128, or the like. For the purposes of this disclosure, a "subject" is an individual who receives medical care, treatment, or consultation from a user. As a non-limiting example, subject may include a patient. For example, and without limitation, subject may include a patient undergoing electrocardiogram using ECG machine 140 or echocardiogram using echocardiogram device 142. In some embodiments, apparatus 100 may include an ECG machine 140 and/or echocardiogram device 142.

With continued reference to FIG. 1, for the purposes of this disclosure, "invasive measurement machine-learning model" is a computational artifact created to recognize patterns, make decisions, and predict outcomes related to invasive measurement datum based on input data, non-invasive measurement data. As a non-limiting example, invasive measurement machine-learning model 128 may include diffusion model, distributive model, neural network, classifier, and the like as described further in detail below.

With continued reference to FIG. 1, memory 108 contains instructions configuring processor 104 to receive non-invasive measurement data 116. For the purposes of this disclosure, "non-invasive measurement data" is information that is obtained through non-invasive measurements. For the purposes of this disclosure, "non-invasive measurement" is a technique used to gather physiological and biological data from subjects without breaking the skin, entering the body or causing any significant discomfort or harm. Non-invasive measurement data 116 includes electrocardiogram (ECG) data 132 and echocardiogram (echo) data 136 as described further in detail below. In some embodiments, non-invasive measurement data 116 may further include blood pressure, pulse oximetry, respiratory rate, temperature, electroencephalogram (EEG), glucose monitoring, cardiac output monitoring such as impedance cardiography or Doppler ultrasound, three dimensional (3D) ultrasound, temporal data, and the like. As a non-limiting example, temporal data may include a sequence of images or measurements captured over a period; such as blood flow, tissue movement, and the like. In some embodiments, non-invasive measurement data 116 may further include information obtained from a survey. As used in this disclosure, a "survey" is a data collection tool in which a list of questions is used to gather information about a subject.

With continued reference to FIG. 1, for the purposes of this disclosure, "electrocardiogram data" is recorded information of the electrical activity of the heart of a user. In one or more embodiments, ECG data 132 may include a matrix having a plurality of electrocardiogram signals and/or associated time variables. A "matrix" for the purposes of this disclosure is an array of numbers or characters arranged in rows or columns which are used to represent an object or properties of the object. For example, and without limitation, a matrix may be used to describe linear equations, differential equations, in a two-dimensional format. In another non limiting example, a matrix may be used to create graphs based on data points, generate statistical models and the like. In one or more embodiments, matrix may include a plurality of electrocardiogram signals associated with a plurality of time variables. As used in the current disclosure, a "electrocardiogram signal" is a signal representative of electrical activity of heart. The ECG signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. The ECG signal may help diagnose various heart conditions, such as arrhythmias, myocardial infarction (heart attack), conduction abnormalities, and electrolyte imbalances. In one or more embodiments, ECG signals may be received by one or more electrodes connected to the skin of an individual. In one or more embodiments, ECG signals may represent depolarization and repolarization occurring in the heart. In one or more embodiments, ECG signals may be captured periodically. For example, and without limitation, every second, every millisecond and the like.

With continued reference to FIG. 1, for the purposes of this disclosure, "echo data" is data collected by an echocardiogram device 142 during an imaging process. As a non-limiting example, echo data 136 may include two dimensional (2D) images of an object of interest and surroundings. In some embodiments, receiving echo data 136 may include receiving echo data 136 from a plurality of echocardiogram devices 142. For the purposes of this disclosure, an "echocardiogram device" is a device that generates information related to sound waves traveled through various tissues and reflected back when the sound waves encounter an object of interest. As a non-limiting example, echocardiogram device 142 may include an ultrasound imaging system (e.g., intracardiac echocardiography (ICE), transthoracic echocardiography (TTE) and transesophageal echocardiography (TEE)). In a non-limiting example, the ultrasound imaging system may include a point-of-care ultrasound (POCUS) (e.g., portable ultrasound) or a conventional ultrasound (e.g., ultrasound that a subject must travel to the ultrasound machine). In some embodiments, conventional ultrasound can assess an anatomical region using predefined parameters and measurements to provide a diagnosis while POCUS can assess one part of the body at a time; this may allow user to answer very specific questions in the context of a physical exam and subject history. In some embodiments, echocardiogram device 142 may capture echo data 136 of in different angles or views. For the purposes of this disclosure, an "object of interest" is a particular element or area of interest of a subject. As a non-limiting example, object of interest may include specific organ, body part, or tissue, cyst, or lumps in an organ. For the purposes of this disclosure, an "organ" is a structure within an organism that is composed of multiple types of tissues and performs a specific function or set of functions. As a non-limiting example, organ may include heart, lung, kidney, liver, stomach, brain, and the like. In some embodiments, echocardiogram devices 142 may operate by converting electrical signals into sound waves and vice versa, capturing 2D ultrasound images of an object of interest.

With continued reference to FIG. 1, in one or more embodiments, each ECG signal may contain an associated time variable. "Time variable" for the purposes of this disclosure is information indicating the time at which a particular ECG signal or EGM signal was received. For example, and without limitation, time variable may include, 5 ms, 10 ms, 15 ms, and the like. In one or more embodiments, each ECG signal may contain a time variable. In one or more embodiments, time variable may increase in given increments, such as for example, in increments of 5 ms, wherein a first time variable may include 5 ms and a second time variable may include 10 ms. In one or more embodiments, a combination of a plurality of ECG signals and correlated time variable may be used to generate a graph illustrating the heart functions of an individual. In one or more embodiments, matrix may include a plurality of ECG signals and correlated time variable during a given time frame such as, for example, over the span of a second, a minute, an hour, and the like. In one or more embodiments, ECG signals may be captured as voltages, such as millivolts or microvolts.

With continued reference to FIG. 1, in some embodiments, apparatus 100 may include a subject database 124. As used in this disclosure, "subject database" is a data store configured to store data associated with a subject. As a non-limiting example, subject database 124 may store invasive measurement training data 112, inputs and outputs of invasive measurement machine-learning model 128, non-invasive measurement data 116, fused non-invasive measurement datum 118, invasive measurement datum 120, and the like. In one or more embodiments, subject database 124 may include inputted or calculated information and datum related to subjects. In some embodiments, a datum history may be stored in subject database 124. As a non-limiting example, the datum history may include real-time and/or previous inputted data related to subjects. As a non-limiting example, subject database 124 may include instructions from a user, who may be an expert user, a past user in embodiments disclosed herein, or the like, where the instructions may include examples of the data related to subjects.

With continued reference to FIG. 1, in some embodiments, processor 104 may be communicatively connected with subject database 124. For example, and without limitation, in some cases, subject database 124 may be local to processor 104. In another example, and without limitation, subject database 124 may be remote to processor 104 and communicative with processor 104 by way of one or more networks. The network may include, but is not limited to, a cloud network, a mesh network, and the like. By way of example, a "cloud-based" system can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. The network may use an immutable sequential listing to securely store subject database 124. An "immutable sequential listing," as used in this disclosure, is a data structure that places data entries in a fixed sequential arrangement, such as a temporal sequence of entries and/or blocks thereof, where the sequential arrangement, once established, cannot be altered or reordered. An immutable sequential listing may be, include and/or implement an immutable ledger, where data entries that have been posted to the immutable sequential listing cannot be altered.

With continued reference to FIG. 1, in some embodiments, subject database 124 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described in this disclosure. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, in some embodiments, processor 104 may receive non-invasive measurement data 116 from remote device 144. For the purposes of this disclosure, a "remote device" is an external device to processor 104. In some embodiments, remote device 144 may include any device a user can use to input data into apparatus 100. As a non-limiting example, remote device 144 may include a laptop, desktop, tablet, mobile phone, smart phone, smart watch, smart headset, or things of the like. For the purposes of this disclosure, a "user" is any person, individual, organization or entity that is using or has used an apparatus. As a non-limiting example, user may include a physician, clinician, nurses, doctors, medical professionals, hospitals, medical organization, and the like. In some embodiments, remote device 144 may include an interface configured to receive inputs from user. In some embodiments, user may manually input any data into apparatus 100 using remote device 144. In some embodiments, user may have a capability to process, store or transmit any information independently.

With continued reference to FIG. 1, processor 104 may receive Non-invasive measurement data 116 using an application programming interface (API). As used in the current disclosure, an "application programming interface" is a software interface for two or more computer programs to communicate with each other. As a non-limiting example, API may include EHR APIs, telemedicine APIs, and the like. An application programming interface may be a type of software interface, offering a service to other pieces of software. In contrast to a user interface, which connects a computer to a person, an application programming interface may connect computers or pieces of software to each other. An API may not be intended to be used directly by a person (e.g., end user) other than a computer programmer who is incorporating it into the software. An API may be made up of different parts which act as tools or services that are available to the programmer. A program or a programmer that uses one of these parts is said to call that portion of the API. The calls that make up the API are also known as subroutines, methods, requests, or endpoints. An API specification may define these calls, meaning that it explains how to use or implement them. One purpose of API may be to hide the internal details of how a system works, exposing only those parts a programmer will find useful and keeping them consistent even if the internal details later change. An API may be custom-built for a particular pair of systems, or it may be a shared standard allowing interoperability among many systems. The term API may be often used to refer to web APIs, which allow communication between computers that are joined by the internet. API may be configured to query for web applications in order to retrieve non-invasive measurement data 116 to another web application, database (e.g., subject database 124), medical center subject portal, and the like. An API may be further configured to filter through web applications according to a filter criterion. In this disclosure, "filter criteria" are conditions the web applications must fulfill in order to qualify for API. Web applications may be filtered based on these filter criteria. Filter criteria may include, without limitation, types of medical facilities, location of the medical facility, and the like.

With continued reference to FIG. 1, in some embodiments, processor 104 may receive non-invasive measurement data 116 from at least a sensor 148. For the purposes of this disclosure, a "sensor" is a device that produces an output signal for the purpose of sensing a physical phenomenon. As a non-limiting example, sensor 148 may include an ECG machine 140. For the purposes of this disclosure, an "ECG sensor" is a device that detects and records the electrical signals produced by the heart during each heartbeat electrocardiogram. For the purposes of this disclosure, an "electrode" is a conductive material or element that facilitates the transmission and reception of electrical signals associated with ultrasound waves. In a non-limiting example, electrode may detect and record electrical activity; for instance, but not limited to, the heart's electrical signals (e.g., ECG signals). In some embodiments, ECG machine 140 may generate a lead system and collect electrical signals using the leads. For the purposes of this disclosure, a "lead system" is the specific electrode placements on the body and the corresponding electrical views of the heart's activity they provide. ECG signals may be collected using lead systems including between 1 to 12 leads. As a non-limiting example, ECG signals may be collected using 1, 2, 3, 4, 5, 6, 7 and/or 12 lead systems. In some embodiments, ECG machine 140 may include 12 lead ECG. In some embodiments, a single-lead ECG may correspond to one of the leads of a 12-lead ECG. For example, and without limitation, one of the leads of the 12-lead ECG to which the single-lead corresponds may be Lead 1, Lead 2, Lead 3, AvF, AvL, AvR, or V1-V6. As another non-limiting example, sensor 148 may include EEG sensor, pulse oximeter, blood pressure monitor, glucose sensor, temperature sensor, wearable fitness tracker, or the like.

With continued reference to FIG. 1, in some embodiments, processor 104 may receive non-invasive measurement data 116 from a wearable device 152. A "wearable device," as used in this disclosure, is a device on a subject that collects non-invasive measurement data from the subject, where "on the subject" indicates that the device is portable and is either worn on the subject, inside the subject, in contact with the subject, or in close proximity to the subject. In some embodiments, wearable device 152 may incorporate sensor 148, ECG machine 140, or echocardiogram device 142. As a non-limiting example, wearable device 152 may include a smart watch, vest, and the like. Non-invasive measurement data 116 may include data generated, collected, and/or transmitted by the wearable device 152 and may include wearables worn by the user such as an accelerometer, pedometer, gyroscope, fitness trackers, force monitors, motion sensors; wearables in contact with a user's skin such as in electrocardiography (ECG), electrooculography (EOG), bioimpedance, blood pressure and heart rate monitoring, oxygenation data, biosensors, eye tracking system; wearables that may be placed inside and/or within a user, and/or devices that may be adapted to be placed outside of the user but aimed at collecting data pertaining to the user. Wearable devices 152 may be any devices capably and useful in acquiring, measuring, and/or transmitting non-invasive measurement data 116; body measurements and calculates related to human characteristics.

With continued reference to FIG. 1, memory 108 contains instructions configuring processor 104 to fuse ECG data 132 and echo data 136 into a fused non-invasive measurement datum 118. For the purposes of this disclosure, a "fused non-invasive measurement datum" is a data element derived from combining multiple non-invasive measurements. As a non-limiting example, fused non-invasive measurement datum 118 may include a vector, and the like. Fusing ECG data 132 and echo data 136 may involve combining these two different types of data. In a non-limiting example, electrocardiogram feature 156 extracted from ECG data 132 and echocardiogram feature 160 extracted from echo data 136 may be concatenated to form a single, unified feature vector; this combined feature vector may encompass both the temporal characteristics of ECG and the spatial information from echo images. For example, and without limitation, if ECG feature 156 includes 64-dimensional vector and echo feature 160 includes 128-dimensional vector, fused non-invasive measurement datum 118 may include 192-dimensional vector that combines temporal (ECG) and spatial (Echo) information.

With continued reference to FIG. 1, in some embodiments, processor 104 may be configured to extract electrocardiogram (ECG) feature 156 from ECG data 132 and echocardiogram (echo) feature 160 from echo data 136 to fuse them. "ECG feature," for the purpose of this disclosure, is a characteristic or attribute derived from ECG data. ECG feature 156 may be quantifiable. ECG feature 156 may provide information regarding electrical activity and functioning of subject's heart. Exemplary ECG feature 156 may include, without limitation, heart rate, PR interval, QT internal, ST segment, and/or the like. As another non-limiting example, ECG features 156 may include several distinct waves and intervals, each representing a different phase of the cardiac cycle, such as P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. "Echo feature," for the purpose of this disclosure, is a characteristic or attribute derived from echo data. As a non-limiting example, echo feature 160 may include chamber size and volume, wall thickness measurements valve morphology, ejection fraction, Doppler flow measurements, regional wall motion, pericardial effusion, and the like.

With continued reference to FIG. 1, processor 104 may be configured to perform one or more feature extraction algorithms to identify ECG feature 156 or echo feature 160. In some embodiments, one or more feature extraction algorithms may be designed to isolate and quantify specific characteristics or markers from signals (e.g., ECG signal or echo signal). Processor 104 may be configured to predict at least one ECG feature 156 or echo feature 160 as a function of ECG data 132 or echo data 136 using the trained models upon receipt of the ECG data 132 or echo data 136. As a non-limiting example, generative model may include a deep learning model trained on ECG signals may be configured to predict ECG feature 156 such as heart rate variability (HRV) or the presence of arrhythmias without needing to extract these features from ECG data 132. In a non-limiting example, generative model may include Naive Bayes, Hidden Markov Models (HMM), Gaussian Mixture Models (GMM), Generative Adversarial Networks (GANs), Variational Autoencoders (VAEs), and the like.

With continued reference to FIG. 1, in some cases, feature extraction algorithms may include model-based approaches. For instance, and without limitation, echo feature 160 may be identified as a function of echo data 136 using generative model, wherein generative model may include one or more models configured to extract detailed spatial hierarchies from the received imaging signal (e.g., echo signal). As a non-limiting example, one or more convolution neural networks (CNNs) may be employed to process imaging signal. In some cases, receiving echo signal may include receiving echo signals sequences including temporal dimensions at CNNs. In some cases, CNNs may include 3D CNNs or CNNs combined with RNN. Additionally, or alternatively, at least one echo feature 160 may be predicted based on echo data 136. One or more machine learning models may be trained on example echo data 136 or ECG data 132 and associated example ECG features 156 or echo features 160. In some cases, one or more feature learning algorithms (i.e., unsupervised learning) such as clustering algorithms may be applied to non-invasive measurement data 116.

With continued reference to FIG. 1, in one or more embodiments, processor 104 may be configured to identify a plurality of ECG feature 156 or echo features 160 as a function of ECG data 132 or echo data 136 respectively. In some cases, plurality of ECG feature 156 or echo features 160 may be evaluated based on a set of pre-determined criteria to ascertain, for example, their clinical significance or relevance in the context of subject diagnosis and healthcare. In one embodiment, set of pre-determined criteria may be used to differentiate between clinically significant abnormalities that necessitate medical intervention and minor anomalies that may not impact subject's health. As a non-limiting example, processor 104 may be configured to filter plurality of ECG features 156 according to one or more pre-determined criteria. In some cases, ECG feature 156 or echo features 160 that significantly deviate from established normal ranges for subject's demographic (age, gender, etc.), identification of ECG feature 156 or echo features 160 that correspond to known medical conditions or risk factors, ECG feature 156 or echo features 160 persist over multiple readings or show a consistent trend over time, ECG feature 156 or echo features 160 that correlate with subject-reported symptoms, ECG feature 156 or echo features 160 indicating conditions with severe outcome or higher risk of progression, ECG feature 156 or echo features 160 that influence treatment decisions (including choice of medication, necessity for surgery, other medical inventions etc.) and the like may be flagged.

With continued reference to FIG. 1, in one or more embodiments, identifying at least one ECG feature 156 or echo feature 160 may include extracting ECG features 156 or echo features 160 from ECG data 132 or echo data 136, ranking the plurality of ECG features 156 or echo features 160 based on set of pre-determined criteria, and identifying the at least one ECG feature 156 or echo features 160 based on the rank of the plurality of ECG features 156 or echo features 160. As a non-limiting example, ECG features 156 or echo features 160 may be processed and filtered, as described above, based on one or more pre-determined criteria selected from set of pre-determined criteria according to clinical urgency, diagnostic value, prognostic significance, subject-specific context, symptom frequency and consistency, or any combination thereof. In some cases, processor 104 may implement a specialized ranking algorithm configured to apply one or more pre-determined criteria to ECG feature 156 or echo feature 160. As a non-limiting example, such ranking algorithm may use weighted factors for each criterion based on its clinical importance. In some cases, ranking algorithm may also be configured to adjust calculated ranks based on inter-feature relationships i.e., how presence of one ECG feature 156 or echo features 160 may influence the significance of another ECG feature 156 or echo features 160. In one embodiment, ranking plurality of ECG features 156 or echo features 160 may include prioritizing plurality of ECG features 156 or echo features 160 with ECG features 156 or echo features 160 ranked highest based on selected criteria at the top in a prioritized data structure e.g., a prioritized list. Processor 104 may be configured to select, form prioritized list, ECG features 156 or echo features 160 above certain threshold for further processing as described below. Additional disclosure related to extracting ECG feature 156 and echo feature 160 may be found in Non-provisional application Ser. No. 18/648,250, filed on Apr. 26, 2024, and entitled "APPARATUS (AND/OR METHOD) OF TRAINING A MACHINE-LEARNING MODEL TO GENERATE DETERMINATIONS USING MISMATCHED-CHANNEL SIGNALS,", and Non-provisional application Ser. No. 18/648,059, filed on Apr. 26, 2024, and entitled "APPARATUS AND METHODS FOR GENERATING DIAGNOSTIC HYPOTHESES BASED ON BIOMEDICAL SIGNAL DATA,", the entirety of which is incorporated herein by reference.

With continued reference to FIG. 1, in some embodiments, processor 104 may combine the raw or preprocessed ECG data 132 and echo data 136 before inputting them into a machine learning model. In some embodiments, processor 104 may preprocess ECG signals to remove noise and artifacts through filtering techniques such as low-pass and high-pass filters and echocardiogram images using enhancement processes like normalization and contrast adjustment to ensure high-quality inputs. For ECG data 132, temporal features (e.g., ECG feature 156) such as heart rate, interval durations (PR, QRS, QT), and amplitudes of different waves using techniques like wavelet transform or Fourier transform may be extracted. For echo data, spatial features (e.g., echo feature 160) may be extracted using convolutional neural networks (CNNs), which capture intricate patterns and details within the ultrasound images. Once the features are extracted, ECG feature 156 and echo feature 160 may be concatenated to form a single, unified feature vector. This combined feature vector (e.g., fused non-invasive measurement datum 118) may include both the temporal characteristics of the ECG and the spatial information from the echo images. This fused feature vector may be then fed into a machine learning model, such as a neural network, which can process the combined data to perform tasks such as classification, regression, or anomaly detection (e.g., generation of invasive measurement datum 120).

With continued reference to FIG. 1, in some embodiments, processor 104 may process ECG data 132 and echo data 136 separately using dedicated models before combining their outputs at a later stage in the processing pipeline. In some embodiments, neural network may include transformers, cascaded models, and the like. For instance, convolutional neural networks (CNNs) may process spatial data such as echocardiogram images and recurrent neural networks (RNNs), long short-term memory networks (LSTMs), may handle temporal sequences like ECG signals. The CNN may process echo data 136, extracting spatial features (e.g., echo feature 160) through a series of convolutional and pooling layers, ultimately flattening the data into a feature vector. Simultaneously, the LSTM may process ECG data 132, capturing temporal dependencies and extracting meaningful sequential features (e.g., ECG feature 156). The outputs of these models may be then concatenated or combined in a fusion layer. This intermediate layer may serve as a bridge, integrating the spatial features from the CNN and the temporal features from the LSTM. The combined features may be subsequently passed through additional fully connected layers or other neural network structures (e.g., invasive measurement machine-learning model 128) to make the final prediction or decision (e.g., generation of invasive measurement datum 120).

With continued reference to FIG. 1, in some embodiments, processor 104 may use separate machine learning models for each data type, each trained to make its own diagnostic predictions. For example, one model might analyze ECG data 132 to generate diagnostic datum 164, while another model may process echocardiogram images (e.g., echo data 136) to generate image datum 168.

With continued reference to FIG. 1, memory 108 contains instructions configuring processor 104 to generate at least an invasive measurement datum 120 as a function of fused non-invasive measurement datum 118 using trained invasive measurement machine-learning model 128. For the purposes of this disclosure, an "invasive measurement datum" is a data element related to information that is conventionally obtained through invasive measurements. For the purposes of this disclosure, "invasive measurement" is a technique that requires the insertion of instruments, devices, or substances into a subject's body. As a non-limiting example, invasive measurement may include computed tomography (CT), x-ray, magnetic resonance imaging (MRI), catheterization, and the like. In a non-limiting example, exposure to CT can increase exposure to radiation. In some embodiments, invasive measurement datum 120 may include temporal images and/or temporal blood flow visualizations. As a non-limiting example, invasive measurement datum 120 may include image datum 168, such as CT image, three-dimensional (3D) data structure, diagnostic datum 164, and the like. In some embodiments, invasive measurement datum 120 may be stored in subject database 124. In some embodiments, processor 104 may retrieve invasive measurement datum 120 from subject database 124. In some embodiments, user may manually input invasive measurement datum 120.

With continued reference to FIG. 1, for the purposes of this disclosure, an "image datum" is a data element related to an image that provides information about anatomical structures of a subject. As a non-limiting example, image datum 168 may include pseudo computed tomography (CT) image, pseudo x-ray image, pseudo MRI image, pseudo PET image, pseudo 3D data structure, and the like. For the purposes of this disclosure, a "pseudo image" is a synthetic or artificially constructed image. For the purposes of this disclosure, a "computed tomography image" is a digital representation of the internal structures of the body that can be obtained through the use of X-ray computed tomography. For the purposes of this disclosure, a "pseudo computed tomography image" is a synthetic or artificially constructed digital representation of the internal structures of the body that can be obtained through the use of X-ray computed tomography. As a non-limiting example, CT image may include contrast-enhanced computed tomography (Contrast CT). In some embodiments, invasive measurement datum 120 may be stored in subject database 124. In some embodiments, processor 104 may retrieve invasive measurement datum 120 from subject database 124. In some embodiments, processor 104 may generate image datum 168 using image generative model 170 of invasive measurement machine-learning model 128.

With continued reference to FIG. 1, for the purposes of this disclosure, an "image generative model" is a generative model that generates an image datum. A diffusion model may model and simulate the progressive refinement of image datum 168 through iterative diffusion processes. Diffusion model may capture the transformation of noise into coherent image structures, enabling the generation of high-fidelity synthetic images.

With continued reference to FIG. 1, in some embodiments, diffusion models may operate by iteratively refining an image through a series of steps, starting from pure noise and progressively adding detail until a clear, high-resolution image is formed. This process can be mathematically described using a forward and reverse diffusion process, governed by stochastic differential equations. In the forward diffusion process, noise is gradually added to the image data, transforming an initial image $x_0$ into a series of increasingly noisy images $x_t$ over time t. The process is represented as $x_t = \sqrt{1-\beta_t}x_{t-1}+\sqrt{\beta_t}\epsilon$, where $\beta_t$ is the variance schedule controlling the amount of noise added at each step, and $\epsilon$ is sampled from a standard Gaussian distribution N(0,I).

With continued reference to FIG. 1, in some embodiments, conversely, reverse diffusion process aims to generate a clean image from noise by iteratively denoising the noisy image $x_T$ back to $x_0$. This reverse process is defined by $$x_{t-1} = \frac{1}{\sqrt{1-\beta_t}}\left(x_t - \sqrt{\beta_t}\,\epsilon_\theta(x_t, t),\right.$$

where $\epsilon_\theta(x_t,t)$ is a neural network trained to predict the added noise at each step. The training objective for the model can be expressed as a simplified version of the variational lower bound (ELBO): $L(\theta)=E_{t,x_0,\epsilon}[\|\epsilon-\epsilon_\theta(x_t,t)\|]^2$, where $\|\cdot\|^2$ denotes the mean squared error, and the expectation is taken over the time steps t, original images $x_0$, and noise $\epsilon$.

With continued reference to FIG. 1, in some embodiments, diffusion model can be trained on large datasets of images to learn the underlying distribution of image data, enabling it to generate new images (e.g., image datum 168) that are statistically similar to the training set. The implementation of this model may include initializing with an initial random noise image $x_T \sim N(0,I)$, using a deep neural network $\epsilon_\theta$ (e.g., U-Net) to predict the noise $\epsilon$ at each step, and applying the reverse diffusion equation iteratively from t=T to t=1 to generate the image.

With continued reference to FIG. 1, in some embodiments, the mathematical formalism of the forward process is described by the Itô SDE: $dx_t=\beta_t x_t dt+\sqrt{\beta_t}dW_t$, where $W_t$ is a Wiener process. The reverse process is described by the reverse-time SDE:

$$dx_t = \left(\frac{\beta_t}{\sqrt{1-\beta_t}}x_t - \beta_t\epsilon_\theta(x_t, t)\right)dt + \sqrt{\beta_t}\,d\overline{W}_t,$$

where $\overline{W}_t$ is the reverse Wiener process.

With continued reference to FIG. 1, in one or more embodiments, processor 104 may implement one or more aspects of "generative artificial intelligence (AI)," a type of AI that uses machine learning algorithms to create, establish, or otherwise generate data such as, without limitation, image datum 168 as described herein that is similar to one or more provided training examples. In an embodiment, machine learning module described herein may generate one or more generative machine learning models that are trained on one or more set of example medical images previously generated. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

With continued reference to FIG. 1, in some cases, image generative model 170 may include a generative machine learning model having one or more generative models. As described herein, "generative models" refers to statistical models of the joint probability distribution P(X,Y) on a given observable variable x, representing features or data that can be directly measured or observed and target variable y, representing the outcomes or labels that one or more generative models aims to predict or generate (e.g., image datum 168). In some cases, generative models may rely on Bayes theorem to find joint probability; for instance, and without limitation, Naïve Bayes classifiers may be employed by computing device to categorize input data into different views.

With continued reference to FIG. 1, in a non-limiting example, one or more generative machine learning models may include one or more Naïve Bayes classifiers generated, by processor 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction.

With continued reference to FIG. 1, although Naïve Bayes classifier may be primarily known as a probabilistic classification algorithm; however, it may also be considered a generative model described herein due to its capability of modeling the joint probability distribution P(X,Y) over observable variables X and target variable Y. In an embodiment, Naïve Bayes classifier may be configured to make an assumption that the features X are conditionally independent given class label Y, allowing generative model to estimate the joint distribution as P(X,Y)=P(Y)ΠiP(Xi|Y), wherein P(Y) may be the prior probability of the class, and P(X_i|Y) is the conditional probability of each feature given the class. One or more generative machine learning models containing Naïve Bayes classifiers may be trained on labeled training data, estimating conditional probabilities P(X_i|Y) and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature X_i, sample at least a value according to conditional distribution P(X_i|y). Sampled feature values may then be combined to form one or more new data instance with selected class label y.

With continued reference to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIGS. 3-5.

With continued reference to FIG. 1, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 3 to distinguish between different categories e.g., real vs. fake, or states e.g., TRUE vs. FALSE within the context of generated data such as, without limitations, generated image datum 168, and/or the like. In some cases, processor 104 may implement one or more classification algorithms such as, without limitation, Support Vector Machines (SVM), Logistic Regression, Decision Trees, and/or the like to define decision boundaries.

With continued reference to FIG. 1, in a non-limiting example, generator of GAN may be responsible for creating synthetic data that resembles real medical images. In some cases, GAN may be configured to receive non-invasive measurement data 116 as input and generates corresponding examples of medical images containing information describing heart anatomy in different ICE views. In some cases, processor 104 may be configured to train GAN synthesizing at least an image datum 168 using the trained GAN. In some cases, during synthesizing at least an image datum 168, discriminator of GAN may evaluate the authenticity of the generated content by comparing it to true medical images, for example, discriminator may distinguish between genuine and generated content and providing feedback to generator to improve the model performance. Additionally, or alternatively, GAN may include a conditional GAN as an extension of the basic GAN as described herein that allows for generation of medical images using non-invasive measurement data 116 based on certain conditions or labels. In standard GAN, generator may produce samples from random noise, while in a conditional GAN, generator may produce samples based on random noise and a given condition or label.

With continued reference to FIG. 1, additionally, or alternatively, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space. Additional disclosure related to a generative model may be found in Non-provisional application Ser. No. 18/509,520, filed on Nov. 15, 2023, and entitled "APPARATUS AND METHODS FOR SYNTHETIZING MEDICAL IMAGES,", the entirety of which is incorporated herein by reference.

With continued reference to FIG. 1, in some embodiments, processor 104 may generate a diagnostic datum 164 as a function of non-invasive measurement data 116. For the purposes of this disclosure, a "diagnostic datum" is a data element related to a diagnosis of a subject based on non-invasive measurement data. As a non-limiting example, diagnostic datum 164 may include name of health condition or disease resulted from analyzing non-invasive measurement data 116. For example, and without limitation, diagnostic datum 164 may include atrial fibrillation (AFib), ventricular tachycardia (VT), ventricular fibrillation (VF), arrhythmia, and the like. As another non-limiting example, diagnostic datum 164 may include decision of a need for a surgery or procedure, and the like. In some embodiments, user may manually input diagnostic datum 164. In some embodiments, processor 104 may retrieve diagnostic datum 164 from subject database 124.

With continued reference to FIG. 1, in some embodiments, processor 104 may be configured to generate diagnosis training data. In a non-limiting example, diagnosis training data may include correlations between exemplary non-invasive measurement data and exemplary diagnosis datums. In some embodiments, diagnosis training data may be stored in subject database 124. In some embodiments, diagnosis training data may be received from one or more users, subject database 124, external computing devices, and/or previous iterations of processing. As a non-limiting example, diagnosis training data may include instructions from a user, who may be an expert user, a past user in embodiments disclosed herein, or the like, which may be stored in memory and/or stored in subject database 124, where the instructions may include labeling of training examples. In some embodiments, diagnosis training data may be updated iteratively on a feedback loop. As a non-limiting example, processor 104 may update diagnosis training data iteratively through a feedback loop as a function of non-invasive measurement data 116, ECG data 132, echo data 136, ECG feature 156, echo feature 160, output of invasive measurement machine-learning model 128, subject cohorts 172, and the like. In some embodiments, processor 104 may be configured to generate a diagnosis neural network 176 of invasive measurement machine-learning model 128. For the purposes of this disclosure, a "diagnosis neural network" is a type of artificial neural network designed to generate a diagnostic datum. In a non-limiting example, generating diagnosis neural network 176 may include training, retraining, or fine-tuning diagnosis neural network 176 using diagnosis training data or updated diagnosis training data. In some embodiments, processor 104 may be configured to determine diagnostic datum 164 using diagnosis neural network 176 (i.e. trained or updated diagnosis neural network 176). In some embodiments, generating training data and training machine-learning models may be simultaneous.

With continued reference to FIG. 1, processor 104 may be configured to generate an initial three-dimensional (3D) model 180 of object of interest (e.g., cardiac anatomy). As used in this disclosure, an "initial 3D model" is a foundational representation, capturing the basic geometric and spatial characteristics of an organ in 3D space. In an embodiment, initial 3D model 180 may provide a "starting point" for further refinement and customization, allowing for the incorporation of more detailed and subject-specific information. In some cases, initial 3D model 180 may be generated through a direct 3D reconstruction from a series of (2D) ICE images or fused non-invasive measurement datum 118. Processor 104 may be configured to apply one or more 3D reconstruction algorithms, such as without limitation, marching cubes, contour detection and segmentation, active contour models, and/or the like to create a coherent 3D representation e.g., initial 3D model 180. In some cases, such direct 3D reconstruction may leverage the inherent spatial information within set of images, providing a direct and intuitive way to model the initial 3D model 180 of the heart's structure. In a further embodiment, generic 3D modeling techniques may be applied to create the initial 3D model. In some cases, generic 3D modeling techniques may include surface modeling, solid modeling, or parametric modeling, among others. As an ordinary person skilled in the art, upon reviewing the entirety of this disclosure, will be aware of various 3D reconstruction algorithms may be used by processor 104 to generate initial 3D model 180.

With continued reference to FIG. 1, processor 104 may be configured to refine generated initial 3D model 180 as a function of image datum 168. In a non-limiting embodiment, refining initial 3D model 180 may include utilizing a statistical shape model (SSM). It should be noted that SSM may not be the only method for refining initial 3D model 180. A person of ordinary skill in the art, upon reviewing the entirety of this disclosure, will be aware of various methods, such as, without limitation, mesh smoothing techniques, level set method, physics-based simulation, among others may be implemented, by processor 104, to refine initial 3D model 180 described herein. As used in this disclosure, a "statistical shape model (SSM)" is a data structure representing, including, and/or utilizing a mathematical model that captures principal modes of variation in shape across a population of cardiac anatomies. In some cases, SSM may be constructed by analyzing one or more datasets of shapes and identifying, for example, mean shapes and main modes of variation within the one or more datasets. In a non-limiting example, SSM may start with calculation of at least one mean shape, which represents an average geometry of all the heart shapes in a given dataset, wherein the at least one mean shape may be served as a central reference point for processor 104 to understand different variations.

With continued reference to FIG. 1, processor 104 may be configured to generate a subsequent three-dimensional (3D) model 184 as a function of the refinement. As used in this disclosure, a "subsequent 3D model" refers to a more detailed and accurate 3D representation than an initial 3D data structure. In an embodiment, subsequent 3D model 184 may be derived from initial 3D model 180 and/or image datum 168. In such embodiment, subsequent 3D model 184 may include a deformed initial 3D model 180 and/or image datum 168. Additional disclosure related to generating initial 3D model 180 and/or subsequent 3D model 184 or generating images may be found in Non-provisional application Ser. No. 18/376,688, filed on Oct. 4, 2023, and entitled "APPARATUS AND METHODS FOR GENERATING A THREE-DIMENSIONAL (3D) MODEL OF CARDIAC ANATOMY VIA MACHINE-LEARNING,", Non-provisional application Ser. No. 18/509,520, filed on Nov. 15, 2023, and entitled "APPARATUS AND METHODS FOR SYNTHETIZING MEDICAL IMAGES,", Non-provisional application Ser. No. 18/426,604, filed on Jan. 30, 2024, and entitled "APPARATUS AND METHOD FOR GENERATING A THREE-DIMENSIONAL (3D) MODEL OF CARDIAC ANATOMY BASED ON MODEL UNCERTAINTY, ", Non-provisional application Ser. No. 18/648,176, filed on Apr. 26, 2024, and entitled "APPARATUS AND METHODS FOR VISUALIZATION WITHIN A THREE-DIMENSIONAL MODEL USING NEURAL NETWORKS,", the entirety of which is incorporated herein by reference.

With continued reference to FIG. 1, in some embodiments, processor 104 may generate cohort training data 188. In some embodiments, cohort training data 188 may include correlations between exemplary non-invasive measurement data and exemplary subject cohorts. In some embodiments, processor 104 may train a cohort classifier using cohort training data 188. In some embodiments, processor 104 may classify non-invasive measurement data 116 into one or more subject cohorts 172 using cohort classifier 192. In some embodiments, subject or non-invasive measurement data 116 may be classified to a subject cohort 172 using a cohort classifier 192. Cohort classifier 192 may be consistent with any classifier discussed in this disclosure. Cohort classifier 192 may be trained on cohort training data 188, wherein the cohort training data 188 may include non-invasive measurement data 116 correlated to subject cohorts 172. As a non-limiting example, subject cohorts 172 may be related to subject's age, gender, weight, address, medical history, and the like. In some embodiments, subject or non-invasive measurement data 116 may be classified to a subject cohort 172 and processor 104 may determine non-invasive measurement data 116 based on the subject cohort 172 using a machine-learning module as described in detail with respect to FIG. 3 and the resulting output may be used to update invasive measurement training data 112. In some embodiments, processor 104 may retrain invasive measurement machine-learning model 128 using the updated invasive measurement training data 112.

With continued reference to FIG. 1, processor 104 is configured to transmit non-invasive measurement data 116 to a remote device 144. In some embodiments, processor 104 may generate user interface displaying non-invasive measurement data 116, diagnostic datum 164, image datum 168, and the like to a user. In some embodiments, at least a processor 104 may be further configured to generate a user interface displaying non-invasive measurement data 116, diagnostic datum 164, image datum 168, and the like. For the purposes of this disclosure, a "user interface" is a means by which a user and a computer system interact; for example through the use of input devices and software. A user interface may include a graphical user interface (GUI), command line interface (CLI), menu-driven user interface, touch user interface, voice user interface (VUI), form-based user interface, any combination thereof and the like. In some embodiments, user interface may operate on and/or be communicatively connected to a decentralized platform, metaverse, and/or a decentralized exchange platform associated with the user. For example, a user may interact with user interface in virtual reality. In some embodiments, a user may interact with the use interface using a computing device distinct from and communicatively connected to at least a processor 104. For example, a smart phone, smart, tablet, or laptop operated by a user. In an embodiment, user interface may include a graphical user interface. A "graphical user interface," as used herein, is a graphical form of user interface that allows users to interact with electronic devices. In some embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

Figure 2:
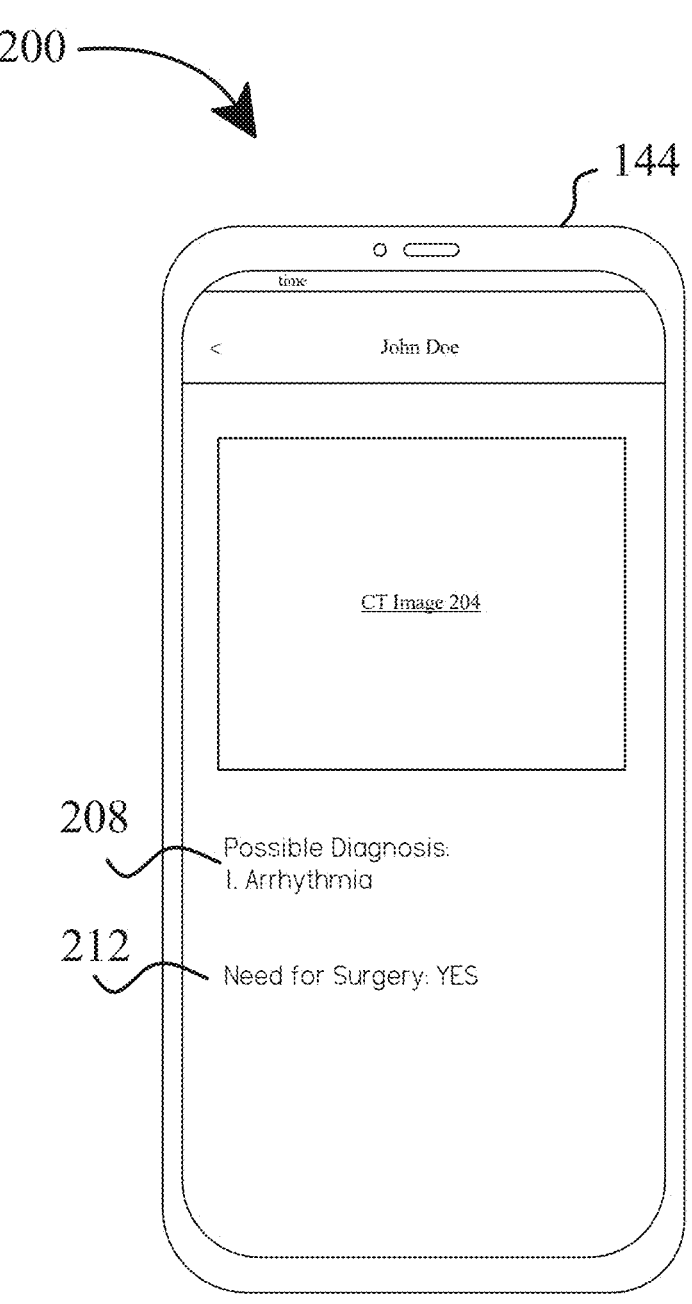
FIG. 2 illustrates an exemplary user interface displaying invasive measurement datums on a remote device.

Referring now to FIG. 2, a configuration of an exemplary user interface 200 displaying invasive measurement datums 120 on a remote device 144 is illustrated. In some embodiments, user interface 200 may display, as shown in FIG. 2, CT image 204 (e.g., image datum 168) that is generated using ECG data 132 and echo data 136. In some embodiments, user interface 200 may display diagnostic datum 164. As a non-limiting example, user interface 200 may display, as shown in FIG. 2, name of condition 208 (e.g., diagnostic datum 164) and necessity of surgery 212 (e.g., diagnostic datum 164).

Figure 3:
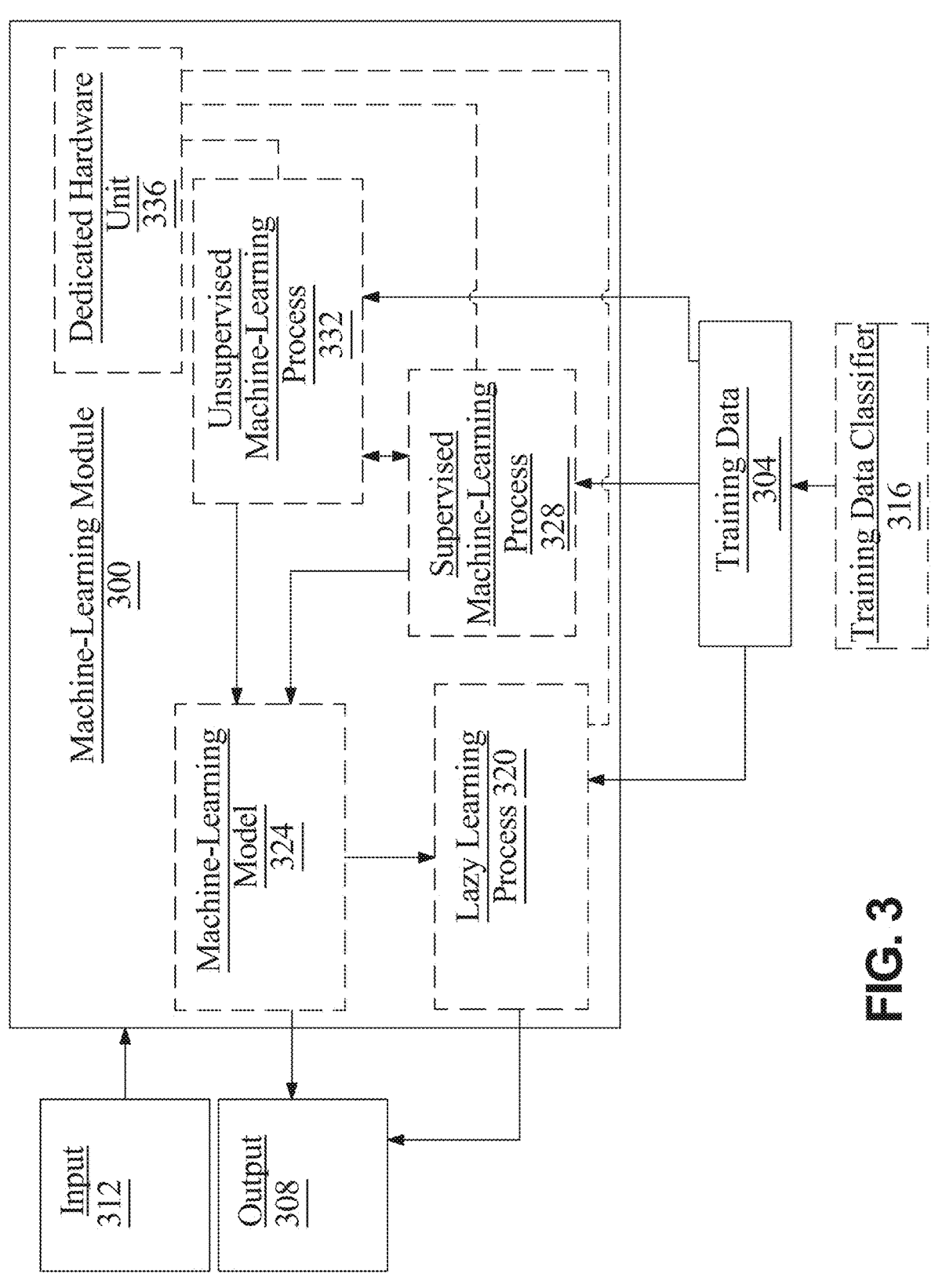
FIG. 3 illustrates a block diagram of an exemplary machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, input data may include non-invasive measurement data 116, ECG data 132, echo data 136, ECG feature 156, echo feature 160, fused non-invasive measurement datum 118, image datum 168, subject cohort 172, initial 3D model 180, and the like. As a non-limiting illustrative example, output data may include ECG feature 156, echo feature 160, fused non-invasive measurement datum 118, invasive measurement datum 120, diagnostic datum 164, image datum 168, subject cohort 172, initial 3D model 180, subsequent 3D model 184, and the like.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to subject cohort. For example, and without limitation, training data classifier 316 may classify elements of training data to subject cohort related to subject's age, gender, weight, health condition, previous medication and treatment, and the like.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below.

Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a set or subset $X_{median}$ and/or interquartile range (IQR), which represents the difference between the 25th percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include non-invasive measurement data 116, ECG data 132, echo data 136, ECG feature 156, echo feature 160, fused non-invasive measurement datum 118, image datum 168, subject cohort 172, initial 3D model 180, and the like as described above as inputs, ECG feature 156, echo feature 160, fused non-invasive measurement datum 118, invasive measurement datum 120, diagnostic datum 164, image datum 168, subject cohort 172, initial 3D model 180, subsequent 3D model 184, and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the clastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
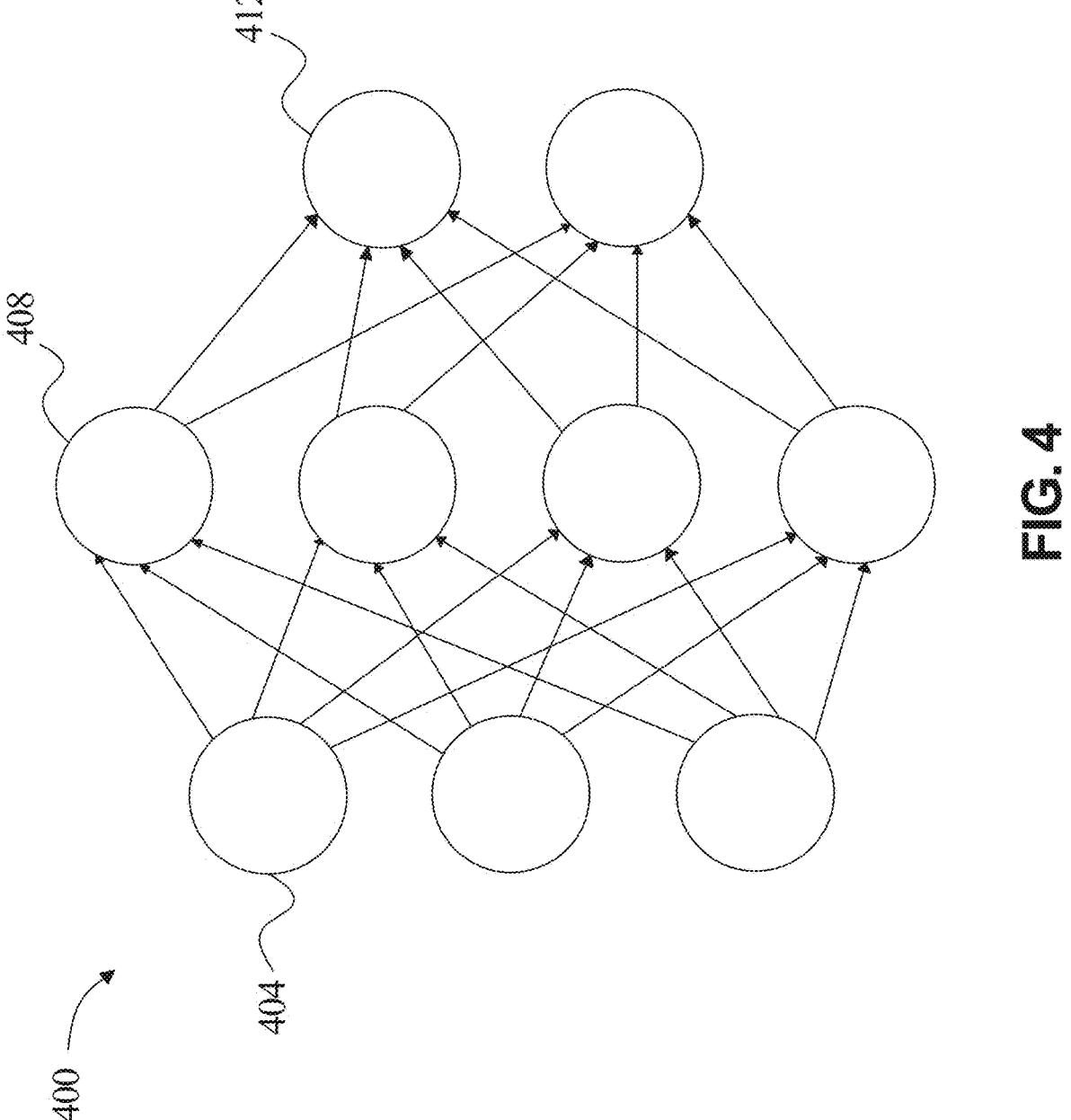
FIG. 4 illustrates a diagram of an exemplary neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
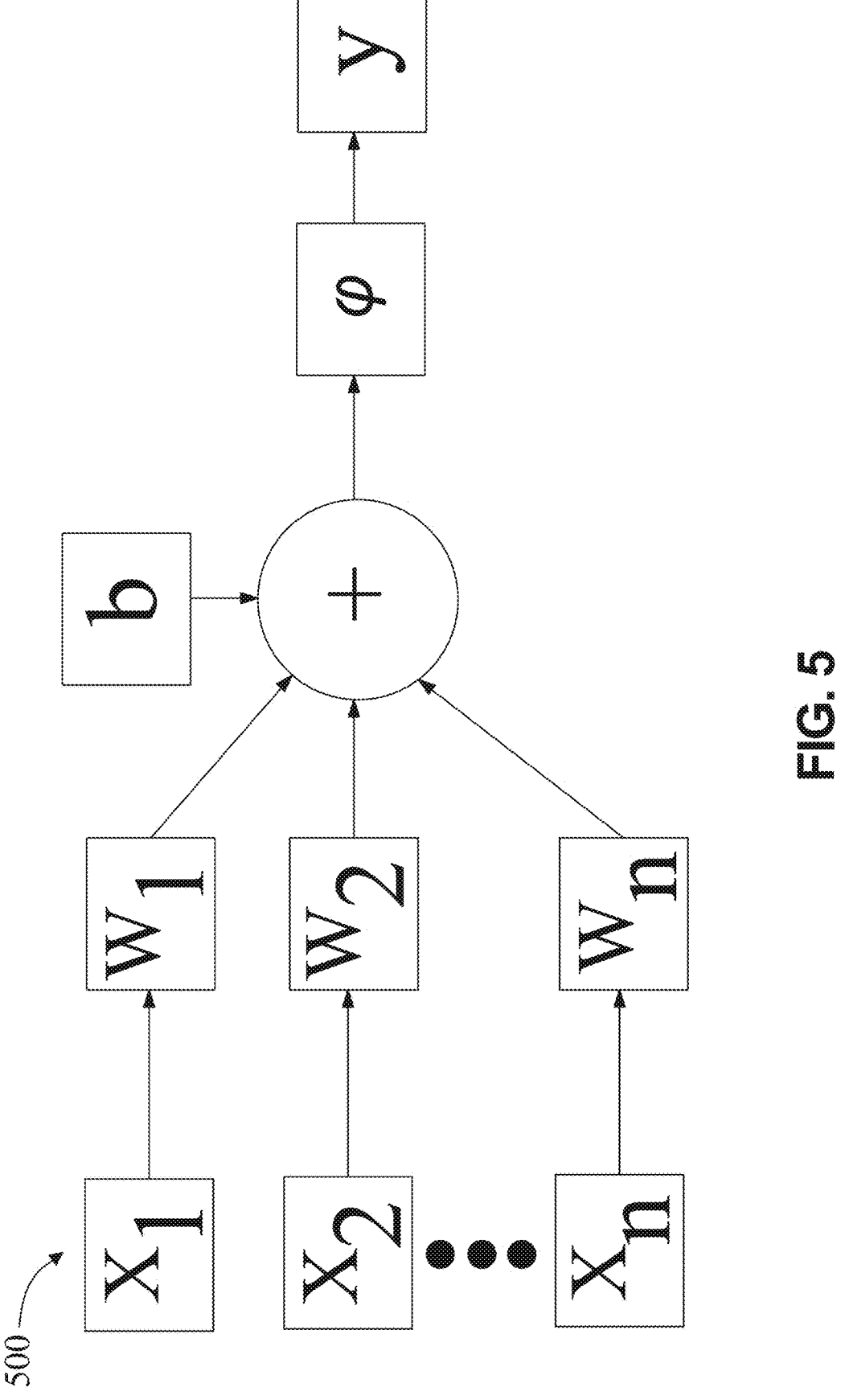
FIG. 5 illustrates a block diagram of an exemplary node in a neural network.

Referring now to FIG. 5 an exemplary embodiment of a node 500 of a neural network is illustrated. A node may include, without limitation, a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0,x)$, a "leaky" and/or "parametric" rectified linear unit function such as $f(x)=\max(ax,x)$ for some a, an exponential linear units function such as $$f(x) = \begin{cases} x & \text{for } x \geq 0 \\ \alpha(e^x - 1) & \text{for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
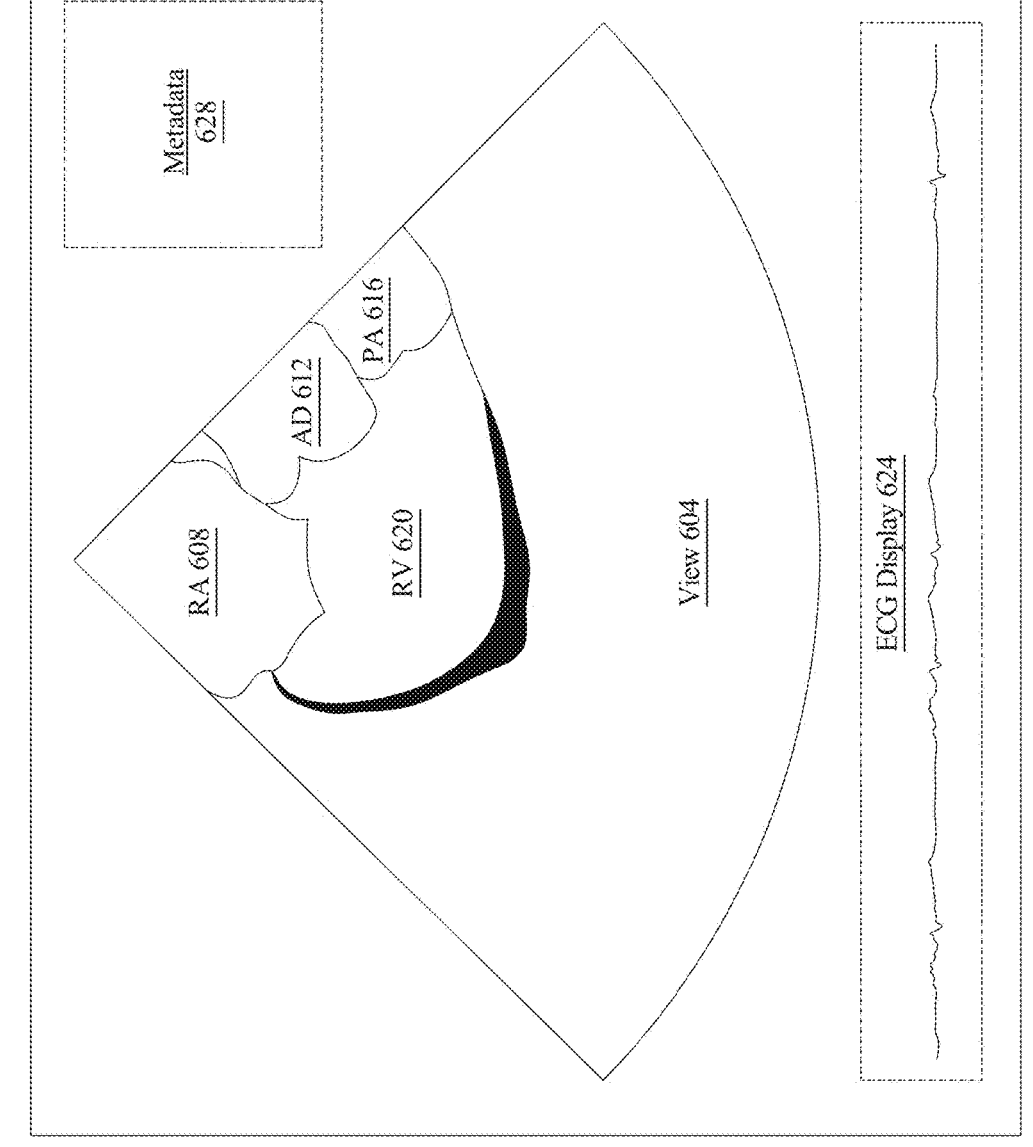
FIG. 6 illustrates an exemplary embodiment of a medical image.

Now referring to FIG. 6, an exemplary embodiment of a medical image 600 is illustrated. As described above with reference to FIG. 1, medical image 600 may include image datum 168 or non-invasive measurement data 116. In some cases, medical image 600 may include a plurality of echocardiography (ICE) images. In an embodiment, ICE image 600 may be real-time, dynamic ultrasound image that provide a (detailed) view 604 of heart's interior structures, including, without limitation, right atrium (RA) 608, anterior descending (AD) 612, pulmonary atresia (PA) 616, and right ventricular (RV) 620.

With continued reference to FIG. 6, in some cases, medical image 600 may include gray scaled image. It should be noted that, in some cases, medical image 600 may be configured to visualize blood flow and/or blood flow patterns within the heart via color doppler. In some cases, resolution and/or clarity of medical image 600 such as ICE image as described herein may be superior to transthoracic or transesophageal echocardiography due to the ICE catheter may be positioned inside the heart, closer to the structures being imaged.

Still referring to FIG. 6, in a non-limiting example, heart chambers 608 may appear as dark, anechoic (black) areas since they are filled with blood, which doesn't reflect ultrasound waves well. Heart walls, valves, and/or other structures may appear as varying shades of gray, depending on their density and composition, in some cases, Color Doppler overlays may show blood flow in different colors, indicating the direction and speed of blood flow. For instance, and without limitation, red may indicate flow towards the probe, while blue may indicate flow away from the probe.

With continued reference to FIG. 6, in a non-limiting embodiment, medical image 600 may be synchronized with ECG data as described above with reference to FIG. 1, allowing for precise timing of cardiac events with anatomical visualization provided by medical image 600 such as ICE image. In some cases, ICE image may include an ECG display 624 configured to display ECG waveform as a continuous line graph at the top, bottom, or side of ICE image. In some cases, specific parts of the cardiac cycle e.g., systole or diastole, may be correlated with visual data from medical image 600.

Additionally, or alternatively, and still referring to FIG. 6, medical image 600 may come with accompanying metadata 628 displayed on the side or corners of medical image 600 as described herein. In some cases, metadata 628 may provide essential contextual information about medical image 600 and/or the corresponding patient. In a non-limiting example, metadata 628 may include patient information (e.g., patient ID, name, DOB, age, gender, and the like), image acquisition details (e.g., date and time, probe type, frequency, depth, gain, and the like), procedure-related information (e.g., procedure name, operator, location, and the like), ECG trace (e.g., ECG data as described above), measurement annotations (e.g., any measurements taken directly on the image e.g., diameter, a value of thickness of a heart wall and the like), image sequence information (e.g., image number, total number of frames, and the like), comments or notes, hospital or clinic information, and/or the like. As an ordinary person skilled in the art, upon reviewing the entirety of this disclosure, will be aware of medical image 600 and various components thereof may be incorporated by apparatus 100 for generating 3D model of cardiac anatomy.

Figure 7:
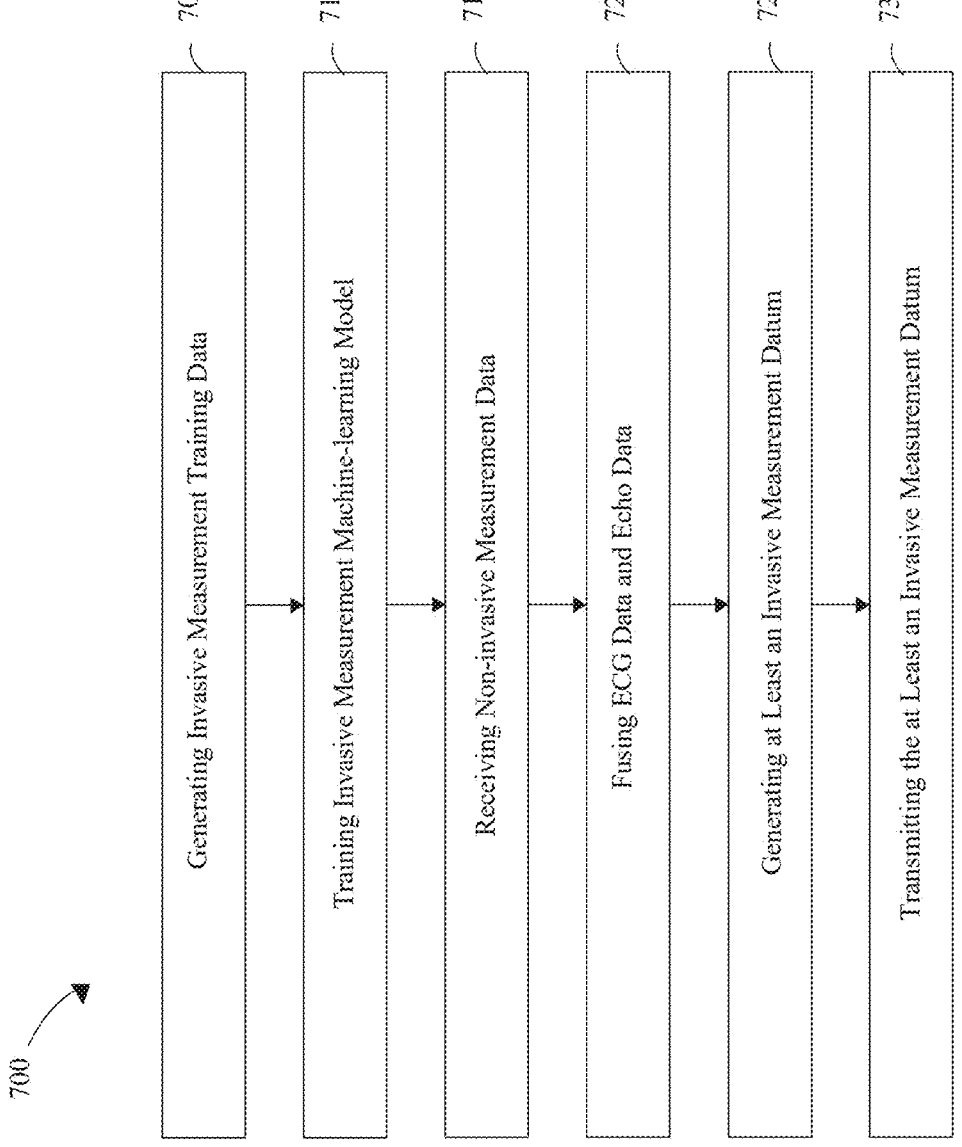
FIG. 7 illustrates a flow diagram of an exemplary method for subject monitoring and diagnosing with non-invasive measures.

Referring now to FIG. 7, a flow diagram of an exemplary method 700 for subject monitoring and diagnosing with non-invasive measures is illustrated. The method 700 contains a step 705 of generating, using at least a processor, invasive measurement training data, wherein the invasive measurement training data includes correlations between exemplary non-invasive measurement data correlated to exemplary invasive measurement datums. This may be implemented as reference to FIGS. 1-6.

With continued reference to FIG. 7, method 700 contains a step 710 of training, using at least a processor, an invasive measurement machine-learning model using invasive measurement training data. This may be implemented as reference to FIGS. 1-6.

With continued reference to FIG. 7, method 700 contains a step 715 of receiving, using at least a processor, non-invasive measurement data, wherein the non-invasive measurement data includes electrocardiogram (ECG) data and echocardiogram (echo) data and the non-invasive measurement data includes information that is obtained through non-invasive measurements. In some embodiments, receiving the non-invasive measurement data may include receiving the non-invasive measurement data from an ECG machine and an echocardiogram device. In some embodiments, receiving the non-invasive measurement data may include receiving the non-invasive measurement data from a wearable device, wherein the wearable device comprises a vest equipped with at least a sensor. These may be implemented as reference to FIGS. 1-6.

With continued reference to FIG. 7, method 700 contains a step 720 of fusing, using at least a processor, ECG data and the data into a fused non-invasive measurement datum. In some embodiments, fusing the ECG data and the echo data may include extracting at least an ECG feature and at least an echo feature from the ECG data and the echo data respectively and fusing the ECG data and the echo data as a function of the at least an ECG feature and the at least an echo feature. In some embodiments, extracting the at least an ECG feature and the at least an echo feature may include extracting the at least an ECG feature using a convolutional neural network and extracting the at least an echo feature using a long short-term memory network. These may be implemented as reference to FIGS. 1-6.

With continued reference to FIG. 7, method 700 contains a step 725 of generating, using at least a processor, at least an invasive measurement datum as a function of a fused non-invasive measurement datum using a trained invasive measurement machine-learning model, wherein the at least an invasive measurement datum includes information that can be obtained through invasive measurements. In some embodiments, generating the at least an invasive measurement datum may include generating an image datum of the at least an invasive measurement datum using an image generative model of the trained invasive measurement machine-learning model, wherein the image datum may include a pseudo computed tomography (CT) image. In some embodiments, generating the image datum may include generating an initial three-dimensional (3D) data structure representing a cardiac anatomy, refining the initial 3D data structure as a function of the image datum and generating a subsequent 3D model of the cardiac anatomy as a function of the refinement. In some embodiments, generating the at least an invasive measurement datum may include generating a diagnostic datum of the at least an invasive measurement datum using a diagnosis neural network of the trained invasive measurement machine-learning model. In some embodiments, generating the at least an invasive measurement datum may include generating cohort training data, wherein the cohort training data may include exemplary non-invasive measurement data correlated to exemplary subject cohorts, training a cohort classifier using the cohort training data, and classifying the non-invasive measurement data into one or more subject cohorts using the trained cohort classifier. In some embodiments, generating the at least an invasive measurement datum may include updating the invasive measurement training data as a function of an output of the trained cohort classifier and generating the at least an invasive measurement datum using the invasive measurement machine-learning model trained with the updated invasive measurement training data. These may be implemented as reference to FIGS. 1-6.

With continued reference to FIG. 7, method 700 contains a step 730 of transmitting, using at least a processor, at least an invasive measurement datum to a remote device. This may be implemented as reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
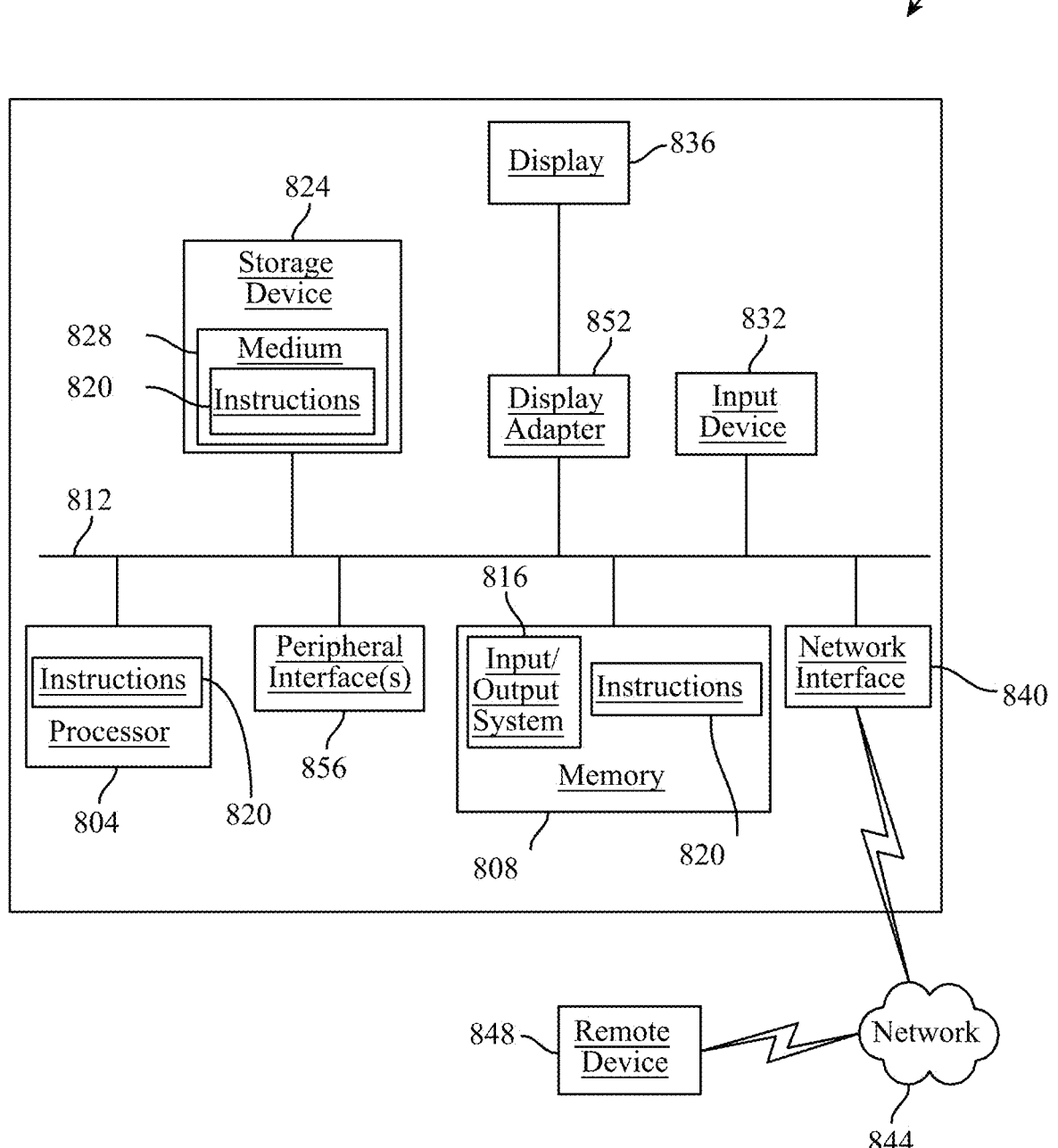
FIG. 8 illustrates a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and memory 808 that communicate with each other, and with other components, via a bus 812. Bus 812 may include any of several types of bus structures including, but not limited to, memory bus, memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display device 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and apparatuses according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for subject monitoring and diagnosing with non-invasive measures, the apparatus comprising:
   at least a processor; and
   a memory communicatively connected to the at least a processor, wherein the memory contains instructions configuring the at least a processor to:
      generate invasive measurement training data, wherein the invasive measurement training data comprises correlations between exemplary non-invasive measurement data correlated to exemplary invasive measurement datums;
      train an invasive measurement machine-learning model using the invasive measurement training data;
      receive non-invasive measurement data of a subject to be monitored and diagnosed, wherein:
         the non-invasive measurement data comprises electrocardiogram (ECG) data received from an ECG machine and echocardiogram (echo) data received from an echocardiogram device; and
         the non-invasive measurement data comprises information that is obtained through non-invasive measurements;
      fuse the ECG data and the echo data into a fused non-invasive measurement datum;
      iteratively update the invasive measurement training data as a function of the non-invasive measurement data;
      update the trained invasive measurement machine-learning model as a function of the iteratively updated invasive measurement training data;
      generate a synthetic computed tomography (CT) image of the subject as a function of the fused non-invasive measurement datum using the updated trained invasive measurement machine-learning model, wherein the synthetic CT image is obtained without exposing the subject to CT or magnetic resonance imaging (MRI) procedures; and
      transmit the synthetic CT image to a remote device.

2. The apparatus of claim 1, further comprising:
   the ECG machine; and
   the echocardiogram device.

3. The apparatus of claim 1, wherein receiving the non-invasive measurement data comprises receiving the non-invasive measurement data from a wearable device, wherein the wearable device comprises a vest equipped with at least a sensor.

4. The apparatus of claim 1, wherein fusing the ECG data and the echo data comprises:

extracting at least an ECG feature and at least an echo feature from the ECG data and the echo data respectively; and
   fusing the ECG data and the echo data as a function of the at least an ECG feature and the at least an echo feature.

5. The apparatus of claim 4, wherein extracting the at least an ECG feature and the at least an echo feature comprises:
   extracting the at least an ECG feature using a convolutional neural network; and
   extracting the at least an echo feature using a long short-term memory network.

6. The apparatus of claim 1, wherein generating the at least an invasive measurement datum comprises generating an image datum of the at least an invasive measurement datum using an image generative model of the trained invasive measurement machine-learning model, wherein the image datum comprises a pseudo computed tomography (CT) image.

7. The apparatus of claim 6, wherein generating the image datum comprises:
   generating an initial three-dimensional (3D) data structure representing a cardiac anatomy;
   refining the initial 3D data structure as a function of the image datum; and
   generating a subsequent 3D model of the cardiac anatomy as a function of the refinement.

8. The apparatus of claim 1, wherein generating the at least an invasive measurement datum comprises generating a diagnostic datum of the at least an invasive measurement datum using a diagnosis neural network of the trained invasive measurement machine-learning model.

9. The apparatus of claim 1, wherein generating the at least an invasive measurement datum comprises:
   generating cohort training data, wherein the cohort training data comprises exemplary non-invasive measurement data correlated to exemplary subject cohorts;
   training a cohort classifier using the cohort training data; and
   classifying the non-invasive measurement data into one or more subject cohorts using the trained cohort classifier.

10. The apparatus of claim 9, wherein generating the at least an invasive measurement datum comprises:
    updating the invasive measurement training data as a function of an output of the trained cohort classifier; and
    generating the at least an invasive measurement datum using the invasive measurement machine-learning model trained with the updated invasive measurement training data.

11. A method for subject monitoring and diagnosing with non-invasive measures, the method comprising:
    generating, using at least a processor, invasive measurement training data, wherein the invasive measurement training data comprises correlations between exemplary non-invasive measurement data correlated to exemplary invasive measurement datums;
    training, using the at least a processor, an invasive measurement machine-learning model using the invasive measurement training data;
    receiving, using the at least a processor, non-invasive measurement data of a subject to be monitored and diagnosed, wherein:
       the non-invasive measurement data comprises electrocardiogram (ECG) data received from an ECG machine and echocardiogram (echo) data received from an echocardiogram device; and the non-invasive measurement data comprises information that is obtained through non-invasive measurements;

fusing, using the at least a processor, the ECG data and the echo data into a fused non-invasive measurement datum;

iteratively updating, using the at least a processor, the invasive measurement training data as a function of the non-invasive measurement data;

updating, using the at least a processor, the trained invasive measurement machine-learning model as a function of the iteratively updated invasive measurement training data;

generating, using the at least a processor, a synthetic computed tomography (CT) image of the subject as a function of the fused non-invasive measurement datum using the updated trained invasive measurement machine-learning model, wherein the at least an invasive measurement datum is obtained without exposing the subject to CT or magnetic resonance imaging (MRI) procedures; and transmitting, using the at least a processor, the synthetic CT image to a remote device.

12. The method of claim 11, wherein receiving the non-invasive measurement data comprises receiving the non-invasive measurement data from a wearable device, wherein the wearable device comprises a vest equipped with at least a sensor.

13. The method of claim 11, wherein fusing the ECG data and the echo data comprises:

extracting at least an ECG feature and at least an echo feature from the ECG data and the echo data respectively; and fusing the ECG data and the echo data as a function of the at least an ECG feature and the at least an echo feature.

14. The method of claim 13, wherein extracting the at least an ECG feature and the at least an echo feature comprises:

extracting the at least an ECG feature using a convolutional neural network; and extracting the at least an echo feature using a long short-term memory network.

15. The method of claim 11, wherein generating the at least an invasive measurement datum comprises generating an image datum of the at least an invasive measurement datum using an image generative model of the trained invasive measurement machine-learning model, wherein the image datum comprises a pseudo computed tomography (CT) image.

16. The method of claim 15, wherein generating the image datum comprises:

generating an initial three-dimensional (3D) data structure representing a cardiac anatomy;

refining the initial 3D data structure as a function of the image datum; and generating a subsequent 3D model of the cardiac anatomy as a function of the refinement.

17. The method of claim 11, wherein generating the at least an invasive measurement datum comprises generating a diagnostic datum of the at least an invasive measurement datum using a diagnosis neural network of the trained invasive measurement machine-learning model.

18. The method of claim 11, wherein generating the at least an invasive measurement datum comprises:

generating cohort training data, wherein the cohort training data comprises exemplary non-invasive measurement data correlated to exemplary subject cohorts;

training a cohort classifier using the cohort training data; and classifying the non-invasive measurement data into one or more subject cohorts using the trained cohort classifier.

19. The method of claim 18, wherein generating the at least an invasive measurement datum comprises:

updating the invasive measurement training data as a function of an output of the trained cohort classifier; and generating the at least an invasive measurement datum using the invasive measurement machine-learning model trained with the updated invasive measurement training data.

* * * * *